United States Patent
Richer-Santos

(10) Patent No.: US 7,045,156 B2
(45) Date of Patent: May 16, 2006

(54) **PROCESS TO PREPARE A SUBSTANCE TO ELIMINATE THE BACTERIA KNOWN AS *HELICOBACTER PYLORI***

(76) Inventor: Eugenio Guillermo Richer-Santos, Nogales #111, Col. Santa Engracia 66267, Garza Garcia, Nuevo Leon (MX)

( * ) Notice: Subject to any disclaimer, the term of this patent is extended or adjusted under 35 U.S.C. 154(b) by 0 days.

(21) Appl. No.: 11/034,718

(22) Filed: Jan. 14, 2005

(65) Prior Publication Data
US 2006/0045921 A1    Mar. 2, 2006

(30) Foreign Application Priority Data
Aug. 31, 2004  (MX) .................... PA/A2004/008417

(51) Int. Cl.
*A61K 35/78*  (2006.01)

(52) U.S. Cl. ........................ 424/725; 424/779

(58) Field of Classification Search ..................... None
See application file for complete search history.

(56) References Cited

OTHER PUBLICATIONS

Navarrete et al. (Phytotherapy Research (1998), vol. 12, pp. 1-4).*

* cited by examiner

*Primary Examiner*—Susan D. Coe
(74) *Attorney, Agent, or Firm*—Breiner & Breiner, L.L.C.

(57) ABSTRACT

A process for the production of a substance to eliminate the bacteria *Helicobacter Pylori*, involving boiling 3 (three) kilos of Cuachalalate (*Amphipterygium adstringens*) crust in sixteen (16) liters of water in a close express pan with a capacity of 21 (twenty-one) liters, for a period of 5 (five) hours, without permitting evaporation. After the boiling period has elapsed, using a filter system, the crust is separated from the resulting liquid or solution. After separating the crust, around six (6) liters of the new solution are obtained. Since the taste of the solution is strong, 1 (one) cubic centimeter of liquid menthol is added in order to make the solution more drinkable. After the prior steps have been taken, the solution must be refrigerated until it is bottled and used. Pills and tablets can be manufactured from the original solution.

3 Claims, No Drawings

# PROCESS TO PREPARE A SUBSTANCE TO ELIMINATE THE BACTERIA KNOWN AS *HELICOBACTER PYLORI*

BACKGROUND OF THE INVENTION

There is a plurality of stomach affections, amongst others: gastritis and peptic ulcers which are caused mainly by a bacteria known as *Helicobacter Pylori* that weakens the inside walls of the stomach making path to the above mentioned affections.

SUMMARY AND OBJECTS OF THE INVENTION

The object of the present invention is mainly to provide a substance that helps to eliminate the bacteria *Helicobacter Pylori* and peptic ulcers by removing the sores or holes in the lining of the stomach through a substance obtained from the crust of a plant called Cuachalalate (*Amphipterygium adstringens*) (an endemic resinous raw plant originally from Mexico that belongs to the Juliananceae family) that when used as medicine, produces the selective destruction of the bacteria *Helicobacter Pylori*, all stomach parasites and cures the sores or holes in the lining of the stomach.

The results and effectiveness of this Cuachalalate (*Amphipterygium adstringens*) crust substance have been clearly demonstrated and proven by clinic tests with X rays before the stomach treatment and again with X rays, after thirty days of treatment, in each individual.

The substance is a natural product that acts as an eliminator of the *Helicobacter Pylori* bacteria and even as a proven method to cure bleeding ulcers if taken as directed, for a 30 days period.

DETAILED DESCRIPTION OF THE PRESENT INVENTION

The process for the production of a substance to eliminate the bacteria *Helicobacter Pylori*, involving boiling 3 (three) kilos of Cuachalalate (*Amphipterygium adstringens*) crust in sixteen (16) liters of water in a close express pan with a capacity of 21 (twenty-one) liters, for a period of 5 (five) hours, without permitting evaporation. After the boiling period has elapsed, using a filter system the crust is separated from the liquid of the resulting solution such that the liquid provides a second solution. Then the second solution is taken out from the pan and with this procedure around six (6) liters of the new, i.e., second, solution are obtained. Since the taste of the solution is strong, 1 (one) cubic centimeter of liquid menthol is added to the second solution; the addition of menthol will help make the substance more drinkable. After the prior steps have been taken, the final solution must be refrigerated until it is bottled and used.

Pills and tablets can be manufactured from the original solution.

I claim:

1. A process for producing a substance to eliminate *Helicobacter Pylori* bacteria comprising:
    boiling three kilos of Cuachalalate crust in sixteen liters of water in a close express pan with a capacity of about twenty-one liters for a period of five hours, without permitting evaporation, to provide a first solution;
    filtering and separating said Cuachalalate crust from liquid in said first solution using a filter system, wherein said liquid provides a second solution;
    removing said second solution from said pan and obtaining a predetermined amount of said second solution; and
    adding about one cubic centimeter of liquid menthol to said second solution to provide a third solution.

2. The process of claim 1, further comprising refrigerating said third solution until said third solution is bottled and/or used.

3. The process of claim 1, further comprising forming said third solution into pills and/or tablets.

* * * * *